(12) United States Patent
Nair et al.

(10) Patent No.: US 12,263,252 B2
(45) Date of Patent: Apr. 1, 2025

(54) BIOTHERAPY FOR VIRAL INFECTIONS USING BIOPOLYMER BASED MICRO/NANOGELS

(71) Applicant: THE FLORIDA INTERNATIONAL UNIVERSITY BOARD OF TRUSTEES, Miami, FL (US)

(72) Inventors: Madhavan Nair, Coral Gables, FL (US); Andrea Raymond, Coconut Creek, FL (US); Arti Vashist, Miami, FL (US)

(73) Assignee: The Florida International University Board of Trustees, Miami, FL (US)

( * ) Notice: Subject to any disclaimer, the term of this patent is extended or adjusted under 35 U.S.C. 154(b) by 0 days.

(21) Appl. No.: 18/950,649

(22) Filed: Nov. 18, 2024

(65) Prior Publication Data
US 2025/0073178 A1 Mar. 6, 2025

Related U.S. Application Data

(60) Division of application No. 17/615,940, filed as application No. PCT/US2020/036292 on Jun. 5, 2020, now Pat. No. 12,144,897, which is a continuation-in-part of application No. 16/432,320, filed on Jun. 5, 2019, now abandoned.

(51) Int. Cl.
*A61K 9/51* (2006.01)
*A61K 9/107* (2006.01)
*A61K 9/20* (2006.01)

(52) U.S. Cl.
CPC .......... *A61K 9/5161* (2013.01); *A61K 9/1075* (2013.01); *A61K 9/2081* (2013.01); *A61K 9/5146* (2013.01)

(58) Field of Classification Search
None
See application file for complete search history.

(56) References Cited

U.S. PATENT DOCUMENTS

| | | | |
|---|---|---|---|
| 4,795,739 A * | 1/1989 | Lifson | A61K 38/16 530/370 |
| 5,336,770 A * | 8/1994 | Shiragami | A61P 31/12 544/276 |
| 5,529,777 A | 6/1996 | Andrianov et al. | |
| 6,777,002 B1 | 8/2004 | Vuaridel et al. | |
| 8,791,069 B1 | 7/2014 | Sung et al. | |
| 2005/0226938 A1 | 10/2005 | Borbely et al. | |
| 2008/0095810 A1 | 4/2008 | Alonso Fernandez et al. | |
| 2009/0202430 A1 | 8/2009 | Hoemann et al. | |
| 2011/0244034 A1 | 10/2011 | Jain et al. | |
| 2012/0145721 A1 | 6/2012 | Cavallin et al. | |
| 2016/0303052 A1 | 10/2016 | Fahmy | |
| 2017/0296577 A1 | 10/2017 | Rigaut et al. | |
| 2019/0175508 A1 | 6/2019 | Bandi et al. | |

FOREIGN PATENT DOCUMENTS

WO 2011004376 A1 1/2011

OTHER PUBLICATIONS

Dalpiaz et al. Antiviral Research 2015 123:146-157 (Year: 2015).*
Ou et al. Journal of Physical Chemistry & Biophysics 2016 7(3)(1000256):1-7 (Year: 2016).*
Selvaraj et al. International Journal of Pharmacy and Pharmaceutical Sciences 2012 4(1):125-132 (Year: 2012).*
Nayak et al. Journal of Microencapsulation 2009 26(3): 214-222 (Year: 2009).*
Giunchedi et al. Pharmacy and Pharmacology Communications. 2000 6(4):149-53 (Year: 2000).*
Wu et al. Chinese Medial Journal 2002 115(10):1569-1572 (Year: 2002).*
Roy et al. (Scholars Academic Journal of Pharmacy 2017 6(1): 34-39 (Year: 2017).*
Angadi, Sudha C. et al. "Interpenetrating polymer network blend microspheres of chitosan and hydroxyethyl cellulose for controlled release of isoniazid." International Journal of Biological Macromolecules, 47(2):171-179, (Year: 2010).
Donalisio, Manuela et al. "Acyclovir-Loaded Chitosan Nanospheres from Nano-Emulsion Templating for the Topical Treatment of Herpesviruses Infections." Pharmaceutics, 10(2):1-12, (Year: 2018).
Fowler, Jeremy N. et al. "Rheology and Microstructure of Shear Thickening Fluid Suspoemulsions." Applied Rheology, 24(4):5-14, (Year: 2014).
Gavegnano, Christina & Schinazi, Raymond "Antiretroviral therapy in macrophages: implication for HIV eradication." Antiviral Chemistry & Chemotherapy, 20:63-78, (Year: 2009).
Landovitz, R.J. et al. "Cabotegravir for HIV prevention in Cisgender Men and Transgender Women." The New England Journal of Medicine, 385(7):595-608, (Year: 2021).
Li, Jiayang et al. "Self-Delivery Multifunctional Anti-HIV Hydrogels for Sustained Release." Advanced Healthcare Materials, 2(12):1586-1590, (Year: 2013).
Mallikarjuna, B. et al. "Chitosan Based Biodegradable Hydrogel Microspheres for Controlled Release of an Anti HIV Drug." Indian Journal of Advances in Chemical Science, 1(3):144-151, (Year: 2013).

(Continued)

*Primary Examiner* — Melissa S Mercier
*Assistant Examiner* — Caralynne E Helm
(74) *Attorney, Agent, or Firm* — SALIWANCHIK, LLOYD & EISENSCHENK

(57) ABSTRACT

A method of treatment or prevention of HIV and other viral infection comprising the administration of a biopolymer-based hydrogel nanoparticles and/or microparticles. In preferred embodiments, the particles comprise chitosan, hydroxyethyl cellulose (HEC), and linseed oil polyol. These biopolymer-based hydrogel nanoparticles and/or microparticles are antiviral agents that can be employed alone or in combination with other drugs for treatment of the viral infection. Further, the pre-treatment with the particles is highly effective at inhibiting viruses. Therefore, this antiviral biopolymer-based hydrogel nanoparticles and/or microparticles may also be employed as a prophylactic.

13 Claims, 9 Drawing Sheets

(56) References Cited

OTHER PUBLICATIONS

Tian, Wenxue et al. "LDH hybrid thermosensitive hydrogel for intravaginal delivery of anti-HIV drugs." Artificial Cells, Nanomedicine, and Biotechnology: An International Journal, 47(1):1234-1240, Apr. 10, 2019.
Vashist, Arti et al. "Interpenetrating biopolymer network based hydrogels for an effective drug delivery system." Carbohydrate Polymers 87(2):1433-1439, (Year: 2012).
Vashist, Arti et al. "Recent trends on hydrogel based drug delivery systems for infectious diseases." Biomaterials Science, 4(11):1535-1553, (Year: 2016).
Vashist, Arti et al. "Development of Multifunctional Biopolymeric Auto-Fluorescent Micro- and Nanogels as a Platform for Biomedical Applications." Frontiers in Bioengineering and Biotechnology, 8(315):1-10, Apr. 2020.
Veiga-Ochoa, Maria-Dolores et al. "Vaginal Formulations for Prevention of Sexual Transmission of HIV." Advances in HIV and AIDS Control, 10:227-248, (Year: 2018).
Zhang, Youwei et al. "Facile fabrication of pH-sentistive core-shell nanoparticles based on HEC and PMAA via template polymerization." European Polymer Journal, 46:1425-1435, (Year: 2010).
Supplementary Search Report issued by the European Patent Office dated Aug. 22, 2023 with respect to parallel European application No. 20818555.3.

* cited by examiner

BIOTHERAPY FOR VIRAL INFECTIONS USING BIOPOLYMER BASED MICRO/NANOGELS

CROSS-REFERENCE TO A RELATED APPLICATION

This application is a divisional application of U.S. application Ser. No. 17/615,940, filed Dec. 2, 2021, which will issue as U.S. Pat. No. 12,144,897 on Nov. 19, 2024, which is a National Stage Application of International Application No. PCT/US2020/036292, filed Jun. 5, 2020; which is a continuation-in-part (CIP) application of U.S. application Ser. No. 16/432,320, filed Jun. 5, 2019, the disclosures of each of which are hereby incorporated by reference in their entirety, including all figures, tables and drawings.

GOVERNMENT SUPPORT

This invention was made with government support under DA040537 and DA037838, awarded by the National Institutes of Health. The government has certain rights in the invention.

BACKGROUND OF INVENTION

Hydrogels are soft materials developed using natural and synthetic polymers that have been explored intensively in biomedical applications. Hydrogels are three-dimensional network of hydrophilic polymers that have the ability to imbibe a large amount of water. Their soft porous structure makes them resemble human tissue, which serves as an excellent candidate to be used in drug delivery and tissue engineering applications.

Hydrogels can be designed and developed in various forms such as films, crystals and particles for drug delivery application. The development of natural polymer based hydrogels for the treatment of various infectious diseases is of great interest in the field of infectious diseases. Hydrogels with microgel and nanogel dimensions show improved characteristics in imaging, therapeutics delivery and tissue engineering.

According to a 2017 UNAIDS report, 36.9 million people worldwide are currently affected with HIV/AIDS, which includes 1.8 million children. Micro/nanogels are promising as the next generation materials for therapeutics. Biopolymers, such as chitosan and hydroxyethyl cellulose, have been explored in formulations that display anti-viral and anti-bacterial properties. Sulfated chitosan derivatives have been prepared that inhibit retrovirus replication. N-carboxymethylchitosan-N, O-sulfate inhibits the synthesis of virus-specific proteins and replication of HIV-1 in cultured T-cells and Rausher murine leukemia virus, displaying no cytotoxicity of chitosan derivative toward the cell cultures. (see Chirkov, *Prikladnaya Biokhimiya i Mikrobiologiya* 2002, 38, 1, 5-13) Hydroxyethyl cellulose gels have been used as a carrier of chloroquine that is stable at ambient tropical conditions for treatment of HIV-1 infection. (see Brouwers et al., *Virology* 2008, 378, 306-10)

Macrophages are the most dominant target of HIV in the central nervous system. The infected macrophages play a very important role in altering the neuronal metabolism. Infected macrophages also play a critical role in activation of CD4 lymphocytes by the production of cytokines and virus proteins such as Nef. In spite of the development of several anti-HIV drugs, there is an intense need of new therapeutics, which can exert less toxicity, better penetration and effective anti-HIV effects on the infected cells or macrophages. Another important challenge is that the only drugs available to interfere with the virus production and release from HIV infected macrophages are protease inhibitors (PIs). The effective dose concentration of PIs is quite high and may lead to a lack of adherence to therapy. Suboptimal dosing can also lead to a resurgence of the viral replication from the chronically infected macrophages and failed therapy.

Recently, auto-fluorescent hydrogel nanoparticles and microparticles based on chitosan and hydroxyethyl cellulose using linseed oil polyol and a crosslinking agent have been designed (U.S. Pat. No. 10,344,100).

BRIEF SUMMARY

The subject invention provides compositions and methods of treatment for viral infections where the treatment involves administering biopolymer-based hydrogel nanoparticles and/or microparticles. In one embodiment, the biopolymer-based hydrogel nanoparticles and/or microparticles comprise one or more biopolymers selected from hydroxylpropylcellulose (HPC), carboxymethyl cellulose (CMC), methyl cellulose (MC), starches, pectin, chitosan, and hydroxyethyl cellulose (HEC). In certain embodiments, the biopolymer-based hydrogel nanoparticles and/or microparticles further comprise a hydrophobic polyol selected from linseed oil polyol, ricinoleic acid, lesquerollic acid, strophantus, coriaria, cardamine impatiens, sebastiana commersoniana and capparis zeylanica. In preferred embodiments, the biopolymer-based hydrogel nanoparticles and/or microparticles comprise chitosan, HEC, and linseed oil polyol.

In one embodiment, administering the treatment involves applying an aqueous suspension comprising the biopolymer-based hydrogel nanoparticles and/or microparticles. The aqueous suspension can be within a water-in-oil emulsion or an oil-in-water emulsion. The aqueous suspension can be applied to a surface prior to contact with a virus-containing fluid or virus. Thus, the biopolymer based hydrogel nanoparticles and/or microparticles can also be used as a prophylactic.

Alternatively, or additionally, a body surface can be treated after contact with a virus. The aqueous suspension can also contain, for example, a second antiviral agent, an antibacterial agent, an antifungal agent, or any combination thereof.

In one embodiment, the method of administration can be by ingesting or inhaling a formulation comprising the biopolymer-based hydrogel nanoparticles and/or microparticles. The formulation can be in the form of a liquid, an aerosol, or a solid device such as a powder, pill, or capsule. The formulation can include a second antiviral agent, an antibacterial agent, an antifungal agent, or any combination thereof. The method of administering can also be by injecting an aqueous suspension containing the biopolymer-based hydrogel nanoparticles and/or microparticles. The injectable suspension can include a second antiviral agent, an antibacterial agent, an antifungal agent, or any combination thereof.

In a specific embodiment, the subject invention provides a formulation for treatment or prevention of an HIV infection, where biopolymer-based hydrogel nanoparticles and/or microparticles comprising chitosan, HEC, and linseed oil polyol is used for the treatment of a viral infection. The formulation can be based on an aqueous suspension comprising the biopolymer-based hydrogel nanoparticles and/or microparticles or can be in the form of a solid powder, pill, or capsule. The formulation can include a second antiviral agent, an antibacterial agent, an antifungal agent, or any combination thereof. The formulation can also include any adjuvant to promote administration of the formulation or augment the activity or characteristics of the formulation.

DETAILED DISCLOSURE

Figure 1A:
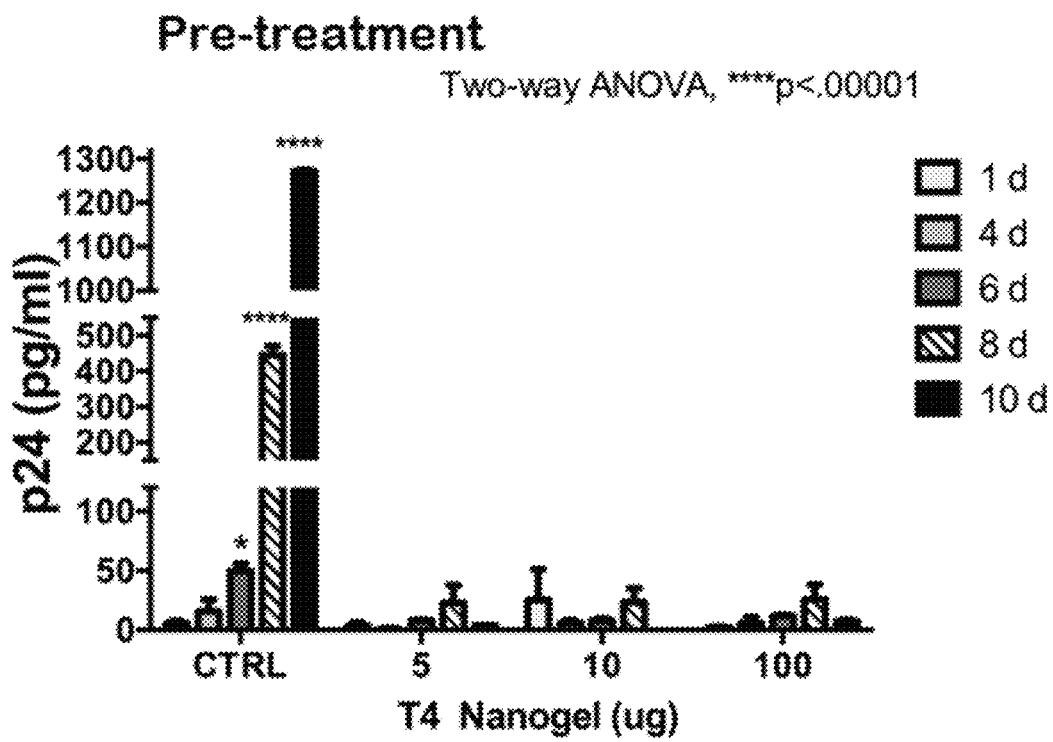
FIG. 1A shows a bar graph for HIV infection as measured by p24 ELISA values 2 hours post-HIV exposure for PHA-stimulated peripheral blood mononuclear cells (PBMCs) ($50 \times 10^6$) infected with HIV (NLAD8 strain) with the plates pretreated for 24 hour pretreatment with nanogel, according to an embodiment of the invention, where culture supernatants were collected 1, 4, 6, 8, and 10 days post infection (dpi).

The subject invention provides compositions and methods for the prevention and/or treatment for viral infections. The subject invention also provides a stable bio-polymeric hydrogel system, which can be sorted to various sizes for diverse biomedical applications.

In one embodiment, the composition of the subject invention comprises hydrogel particles in microscale and/or nanoscale. Advantageously, in preferred embodiments, the hydrogel microparticles and/or nanoparticles have the following features: (i) easy synthesis with high yield; (ii) highly biocompatible to the intracellular environment; (iii) the by-products of the hydrogels are biodegradable and non-toxic to the cellular environment; (iv) have functionality which makes them capable of binding with various bio-actives including drugs, DNA, RNA, proteins, etc.; (v) the biomaterials can be detected in vitro and in vivo; and (vi) the cellular uptake and tracking are feasible.

In one embodiment, the composition according to the subject invention comprises hydrogel microparticles and/or nanoparticles, and optionally a pharmaceutically acceptable carrier. In one embodiment, the hydrogel nanoparticles and/or microparticles can be formed or derived from biopolymers, such as, but not limited to, chitosan, hydroxyethyl cellulose (HEC), hydroxylpropylcellulose (HPC), carboxymethyl cellulose (CMC), methyl cellulose (MC), starches, and pectin.

"Pharmaceutically acceptable carrier" or "pharmaceutically acceptable excipient" includes any and all solvents, dispersion media, coatings, antibacterial and antifungal agents, isotonic, and absorption delaying agents, and the like. The use of such media and agents for pharmaceutically active substances is well known in the art. Except insofar as any conventional media or agent is incompatible with the active ingredient, its use in the therapeutic compositions of the invention is contemplated. Supplementary active ingredients can also be incorporated into the compositions.

Examples of carriers suitable for use in the pharmaceutical compositions are known in the art and such embodiments are within the purview of the invention. The pharmaceutically acceptable carriers and excipients, including, but not limited to, aqueous vehicles, water-miscible vehicles, non-aqueous vehicles, stabilizers, solubility enhancers, isotonic agents, buffering agents, suspending and dispersing agents, wetting or emulsifying agents, complexing agents, sequestering or chelating agents, cryoprotectants, lyoprotectants, thickening agents, pH adjusting agents, and inert gases. Other suitable excipients or carriers include, but are not limited to, dextran, glucose, maltose, sorbitol, xylitol, fructose, sucrose, and trehalose.

In one embodiment, the hydrogel nanoparticles and/or microparticles may further include magnetic nanoparticles (MNP) for example, iron oxide (III) nanoparticles. Copolymers such as sodium alginate and acrylamide may also be combined with one or more biopolymers to form the hydrogel nanoparticles and/or microparticles.

In a specific embodiment, the hydrogel nanoparticles and/or microparticles comprise chitosan, and HEC. Importantly, chitosan can play a significant role in the formation of the crosslinked hydrogel particle. In specific embodiments, chitosan and HEC have a weight ratio of, for example, 1:1, 2:1, 3:1, 4:1, 1:2, 1:3, 2:3, 3:2, 4:3, 3:4, 5:2, 5:3, 5:4, 2:5, 3:5, 4:5, 6:5, 5:6, 7:2, 7:3, 7:4, 7:5, 7:6, 6:7, 5:7, 4:7, 3:7, or 2:7.

Sustainable resource linseed oil-based polyol can also be introduced as an element of hydrophobicity and to facilitate their ability to traverse the blood-brain barrier (BBB). Hydrophobically modified particles by using linseed oil-based polyol develop a surface functionality, which enable them to cross the BBB and enter the brain through the tight junctions.

Elements of hydrophobicity to enhance the stability of hydrogel nanoparticles can be achieved by the addition of linseed oil based polyol or other hydrophobic polyols, such as other vegetable based polyols, including, but not limited to, ricinoleic acid, lesquerollic acid, strophantus, coriaria, cardamine impatiens, sebastiana commersoniana and capparis zeylanica. The inclusion of the polyol results in formation of an interpenetrating network (IPNs) and in this form hydrogel stability can be improved.

Chitosan is a bioactive, biocompatible, biodegradable and nontoxic hydrocolloid, with hemostatic, bacteriostatic, and other properties favorable for a range of industrial and biomedical applications. Chitosan is a polysaccharide comprising 1-4-linked residues of 2-amino-2-deoxy-$\beta$-D-glucose (glucosamine) and 2-acetamido-2-deoxy-$\beta$-D-glucose (N-acetylglucosamine).

In a preferred embodiment, the biopolymer chitosan used to form hydrogel nanoparticles and/or microparticles has a medium molecular weight of 190-310 kDa, 190-300 kDa, 200-300 kDa, 200-290 kDa, 200-280 kDa, 200-270 kDa, 200-260 kDa, 200-250 kDa, 200-220 kDa, 190-200 kDa, or 250-300 kDa.

In specific embodiments, the biopolymer chitosan, when measured for a 1 wt. % solution of the chitosan in 1% acetic acid at 25° C., has a viscosity from about 200 cP to about 800 cP, from about 200 cP to about 700 cP, from about 300 cP to about 700 cP, from about 300 cP to about 600 cP, from about 400 cP to about 600 cP, from about 400 cP to about 500 cP, from about 200 cP to about 300 cP, from about 300 cP to about 400 cP, from about 500 cP to about 600 cP, from about 600 cP to about 700 cP, or from about 700 cP to about 800 cP.

Figure 3:
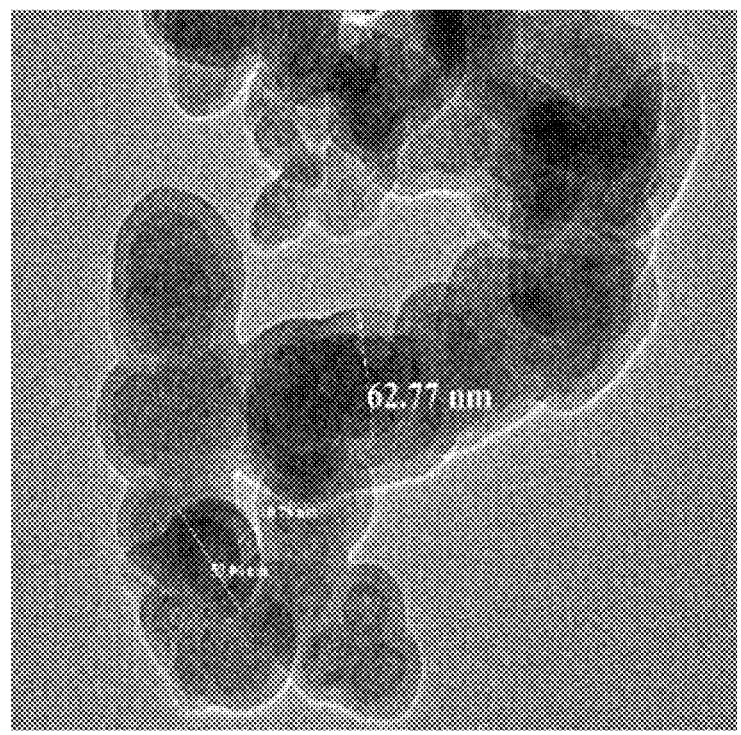
FIG. 3 shows a transmission electron microscopy (TEM) image for the hydrogel nanoparticles.

In one embodiment, the hydrogel nanoparticles and/or microparticles have controlled sizes, e.g., from micro to nano. The hydrogel particles can be designed in various sizes ranging, for example, from about 50 nm to 300 µm, from about 50 nm to 250 µm, from about 50 nm to 200 µm, from about 50 nm to 150 µm, from about 50 nm to 100 µm, from about 50 nm to 50 µm, from about 50 nm to 25 µm, from about 50 nm to 10 µm, from about 50 nm to 5 µm, from about 50 nm to 1 µm, from about 50 nm to 900 nm, from about 50 nm to 800 nm, from about 50 nm to 700 nm, from about 50 nm to 600 nm, from about 50 nm to 500 nm, from about 50 nm to 400 nm, from about 50 nm to 300 nm, from about 50 nm to 200 nm, from about 50 nm to 100 nm, from about 100 nm to 300 µm, from about 150 nm to 300 µm, from about 200 nm to 300 µm, from about 500 nm to 300 µm, from about 1 µm to 300 µm, from about 5 µm to 300 µm, from about 10 µm to 250 µm, from about 20 µm to 200 µm, or from about 50 µm to 100 µm. In a specific embodiment, the hydrogel particles have a core-shell structure with a spherical shape and a size of 60-70 nm (FIG. 3).

In a preferred embodiment, the biopolymer-based hydrogel nanoparticles and/or microparticles comprise chitosan, HEC, and linseed oil polyol. These nanogels are demonstrated to have salient features such as biocompatibility, stability, high cellular uptake by a variety of host cells, and ability to transmigrate across the BBB.

In some embodiments, the hydrogel particles of the subject invention exhibit auto-fluorescence, which can be used for cellular imaging. Auto-fluorescent hydrogels in micro and/or nano scales from completely natural polymers chitosan, HEC and sustainable resource linseed oil based polyol exhibit complete biocompatibility over a concentration range of 10-100 µg/ml using a wide range of host cells, such as, astrocytes, peripheral blood mononuclear cells (PBMCs) and microglia.

These hydrogels display a dynamic wide range of emission wavelengths, 450 to 750 nm and 710 to 810 nm, which permits simultaneous in vivo imaging. Their high stability in aqueous solution at physiological pH, 7.4, allows good shelf-life in solution and in a dry form at room temperature, for at least 6 months, while retaining their auto-fluorescence property.

The use of a wide range of sizes, from microscale to nanoscale, results in cellular uptake and co-localization in ex-vivo studies with PBMC, microglia and astrocytes. Remarkably, the hydrogel particles transmigrate the blood-brain barrier, which allows their use for the drug delivery to the central nervous system.

In one embodiment, the subject invention provides biopolymer-based hydrogel nanoparticles and microparticles of chitosan, hydroxyethyl cellulose (HEC), and linseed oil polyol that have antiviral properties. The subject invention also provides autofluorescent and biocompatible micro/nano gels that have the ability to inhibit the virus replication in, for example, HIV infected macrophages. Advantageously, the micro/nano gels developed using this combination of biopolymers have resulted in inhibiting HIV virus replication in the absence of known anti-retroviral agents.

In one embodiment, the method of the subject invention for prevention and/or treating a viral infection in a subject comprises administering biopolymer-based hydrogel nanoparticles and/or microparticles, or a composition comprising hydrogel nanoparticles and/or microparticles in the subject.

"Subject" refers to an animal, such as a mammal, for example a human. The methods described herein can be useful in both human therapeutics and veterinary applications. In some embodiments, the subject is a mammal (including animal models of disease), and in some embodiments, the subject is human. Non-limiting examples of subjects include canine, porcine, rodent, feline, bovine, poultry, equine, human, and a non-human primate.

In one embodiment, the viral infection may be caused by, for example, RNA viruses including retroviruses (e.g., lentiviruses such as HIV) and coronavirus (e.g., the virus that causes COVID-19). Example of the RNA viruses include, but are not limited to, Orthomyxoviruses, Adenovirus, Hepatitis C Virus (HCV), Zika, the virus that causes COVID-19, Dengue, Ebola, Influenza A/B/C virus, polio measles, primate foamy virus, HIV, SARS-CoV (Severe Acute Respiratory Syndrome-Corona Virus), CoV MERS (Middle East Respiratory Syndrome virus), HCoV-NL63, HCoV-OC43, HCoV-229E, HCoV-HKUI, adult T-cell leukemia virus (ATLV), Human T-cell lymphotropic virus type 1 (HTLV-1), and type II (HTLV-2). Preferably, the virus is HIV-1, or HIV-2. Furthermore, mutated and/or truncated viruses derived from the above viruses are encompassed by the present invention.

Other viruses include, for example, avian leukemia virus, avian sarcoma virus, avian reticuloendotheliosis virus, murine mammary cancer virus, murine leukemia virus, murine sarcoma virus, guinea pig type C virus, hamster type C virus, rat leukemia virus, feline leukemia virus, feline sarcoma virus, feline type C virus, ovine leukemia virus, bovine leukemia virus, swine type C virus, simian leukemia virus, Mason-Pfizer virus, simian sarcoma virus, simian T-lymphotropic virus, baboon type C virus, visna virus, EIAV, spuma virus, ovine progressive pneumonia virus, ovine macdi virus, simian T-lymphotropic virus type III (STLV-III), equine infectious anemia virus, Bovine immunodeficiency virus (BIV), the Feline immunodeficiency virus (FIV), the Simian immunodeficiency virus (SIV), feline Coronavirus (FCoV), and Mouse Hepatitis Virus (MHV-LUC).

In one embodiment, the subject invention provides methods for preventing and/or treating a disease caused by a RNA virus, e.g., retrovirus or coronavirus. The method comprises administering hydrogel nanoparticles and/or microparticles, or a composition comprising hydrogel nanoparticles and/or microparticles.

In one embodiment, the disease may be, for example, Zika, Ebola, Hepatitis C, Influenza, COVID-19, MERS, SARS, AIDS, adult T-cell lymphoma (ATL), Dengue fever, and progressive general lymphadenosis (PGL). Preferably, the disease is AIDS.

The term "treatment" or any grammatical variation thereof (e.g., treat, treating, etc.), as used herein, includes but is not limited to, the application or administration to a subject (or application or administration to a cell or tissue from a subject) with the purpose of delaying, slowing, stabilizing, curing, healing, alleviating, relieving, altering, remedying, less worsening, ameliorating, improving, or affecting the disease or condition, the symptom of the disease or condition, or the risk of (or susceptibility to) the disease or condition. The term "treating" refers to any indication of success in the treatment or amelioration of a pathology or condition, including any objective or subjective parameter such as abatement; remission; lessening of the rate of worsening; lessening severity of the disease; stabilization, diminishing of symptoms or making the pathology or condition more tolerable to the subject; or improving a subject's physical or mental well-being.

The term "prevention" or any grammatical variation thereof (e.g., prevent, preventing, etc.), as used herein, includes but is not limited to, at least the reduction of likelihood of the risk of (or susceptibility to) acquiring a disease or disorder (i.e., causing at least one of the clinical symptoms of the disease not to develop in a patient that may be exposed to or predisposed to the disease but does not yet experience or display symptoms of the disease). The term "prevention" may refer to avoiding, delaying, forestalling, or minimizing one or more unwanted features associated with a disease or disorder, and/or completely or almost completely preventing the development of a disease or disorder and its symptoms altogether. Prevention can further include, but does not require, absolute or complete prevention, meaning the disease or disorder may still develop at a later time and/or with a lesser severity than it would without preventative measures. Prevention can include reducing the severity of the onset of a disease or disorder, and/or inhibiting the progression thereof.

The micro/nanogels according to an embodiment of the invention, display anti-viral properties against HIV primary cellular targets, PBMCs and human astrocytes (HAs), during early and late stages of the HIV life cycle. The level of expression of Capsid antigen (p24) of newly released virions representing late stage in HIV replication was determined using p24 enzyme-linked immunosorbent assay (ELISA) and early stage HIV transcription was measured by quantifying the number of gene transcripts containing the HIV long terminal repeat (LTR) using digital droplet PCR (ddPCR).

Nanogel anti-viral properties were assessed in HIV primary cellular targets, PBMCs and Human astrocytes, during early and late stages in the HIV life cycle. Level of expression of Capsid antigen (p24) of newly released virions representing late stage in HIV replication was determined using p24 ELISA while early stage HIV transcription was measured by quantifying the number of gene transcripts containing the HIV LTR using digital droplet PCR (ddPCR).

Figure 1B:
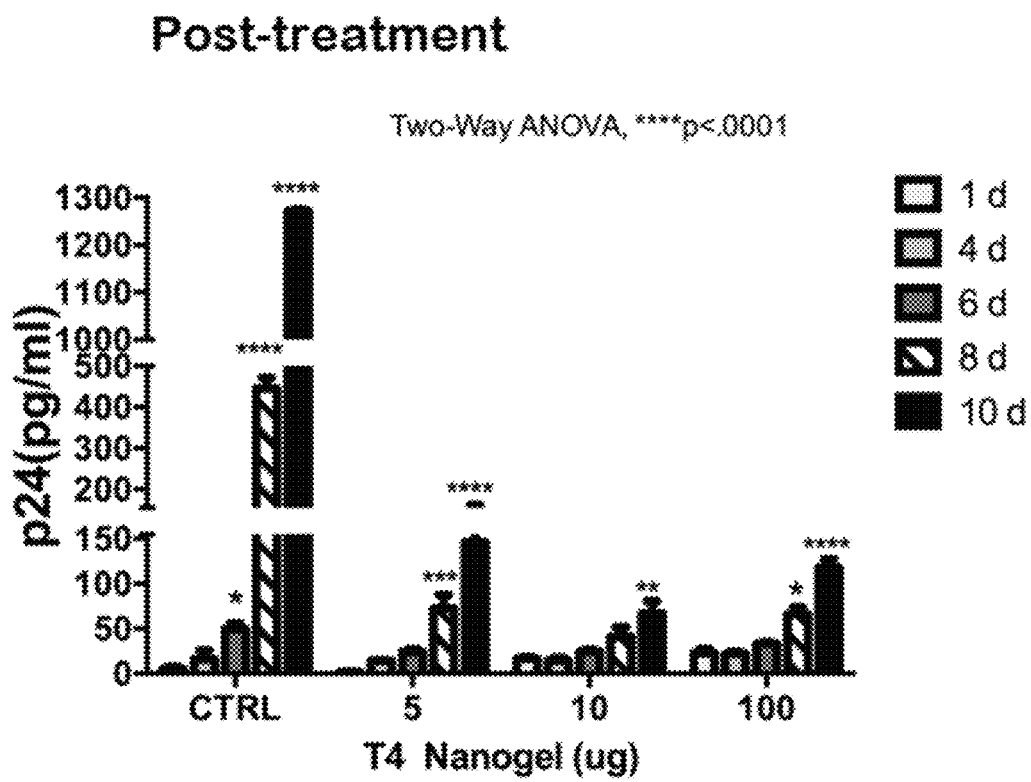
FIG. 1B shows a bar graph for HIV infection as measured by p24 ELISA values 16-18 hours post-nanogel addition to HIV infection for PHA-stimulated PBMCs ($50 \times 10^6$) infected with HIV (NLAD8 strain) 16-18 hours prior to addition of the nanogels, according to an embodiment of the invention, where culture supernatants were collected 1, 4, 6, 8, and 10 dpi.
Figure 1C:
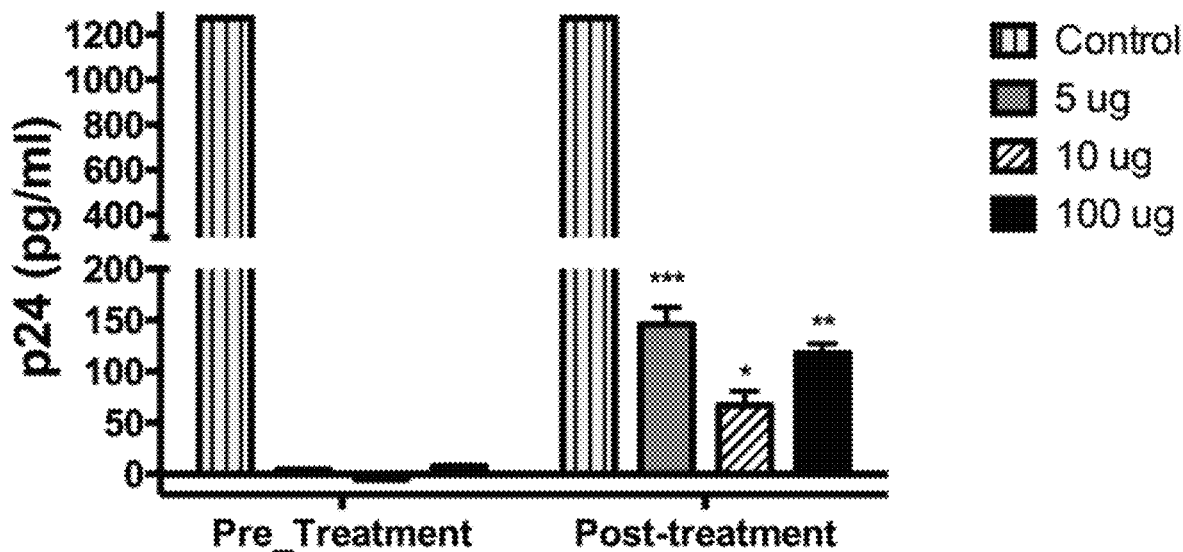
FIG. 1C shows a bar graph for HIV infection as measured by p24 ELISA values 10 dpi for nanogel pre-treated and post-treated with nanogels according to embodiments of the invention.

PBMCs were infected with HIV-1 pre- or post-nanogel administration. Culture supernatants were collected over a 10-day period and p24 ELISA performed to measure viral replication. The data show that pretreatment with increasing doses of T4 nanogel significantly lowered p24 detection levels with little to no p24 released over the 10-day infection period, as shown in FIG. 1A. Nanogel treatment post HIV exposure allowed only low-level HIV replication, and was also able to significantly reduce p24 levels in HIV-infected PBMCs, as shown in FIG. 1B. Pre-exposure to nanogel diminished p24 levels compared to post exposure, as indicated in FIG. 1C, which indicates that nanogel is a novel pre-exposure HIV prophylactic.

Figure 2A:
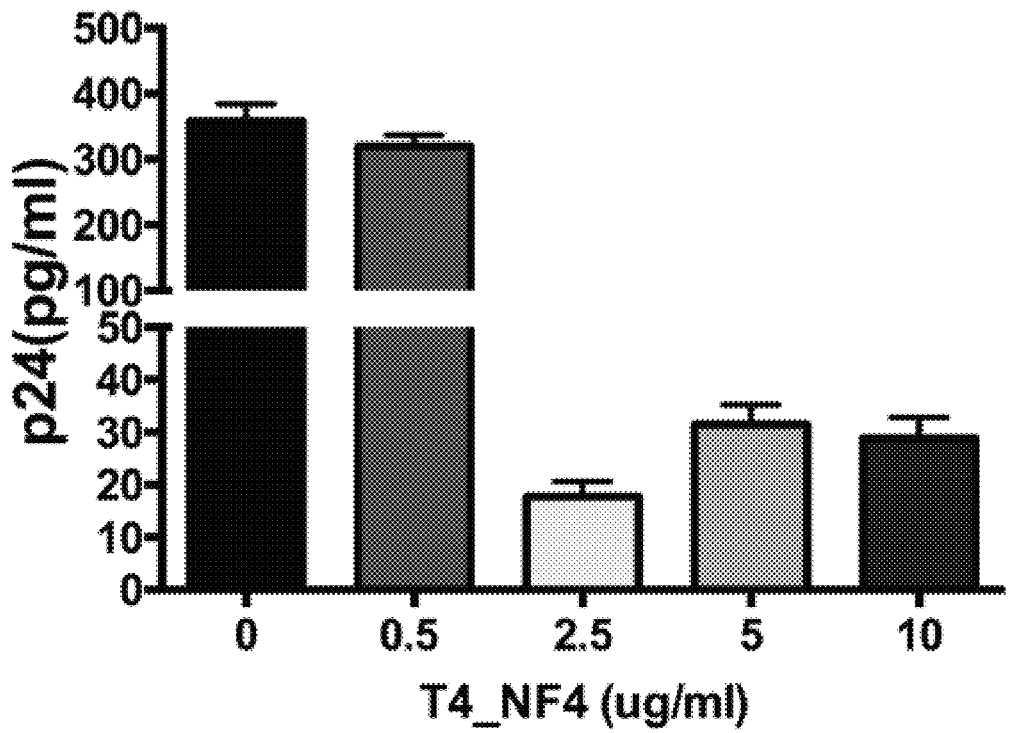
FIG. 2A shows a bar graph for HIV p24 ELISA values for HA infected with HIV (NLAD8 strain) 16 hours post infection for increasing doses of nanogel added to the cell culture with supernatant collected 7 days post infection (dpi).
Figure 2B:
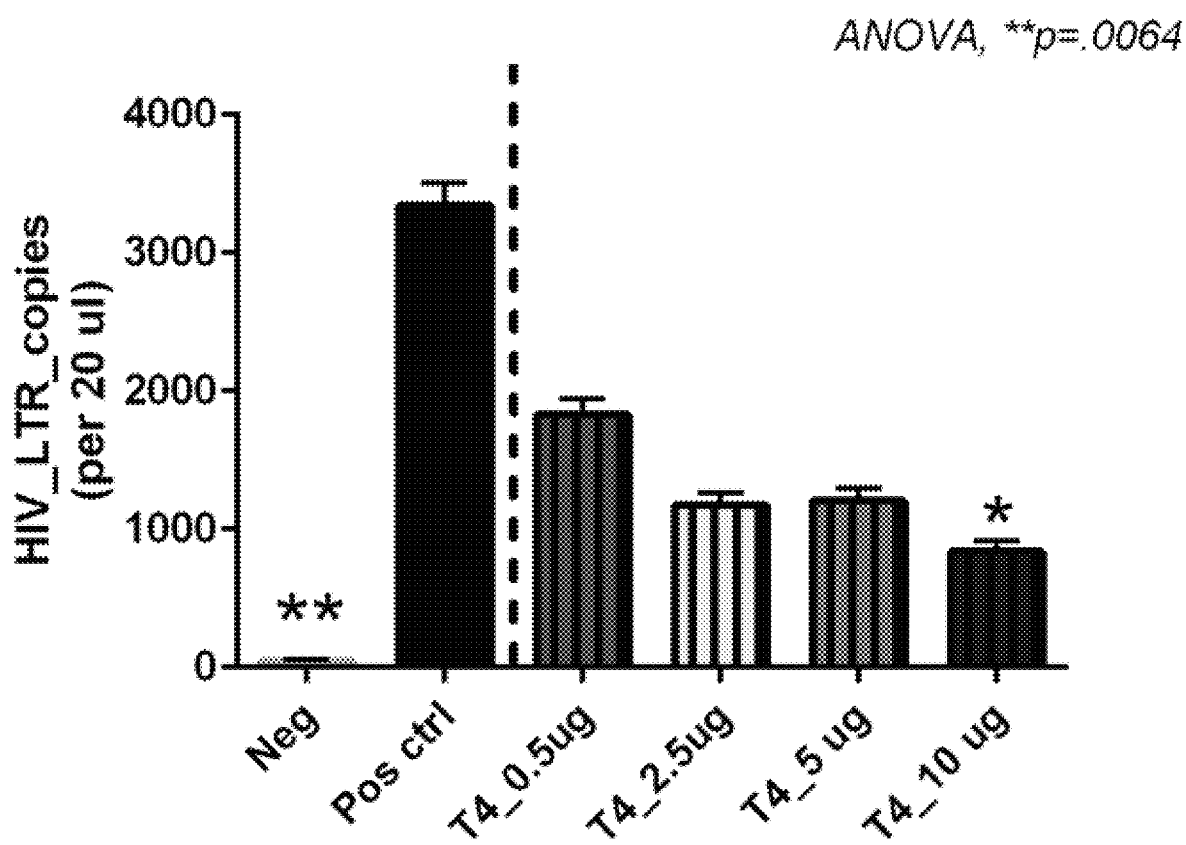
FIG. 2B shows a bar graph of quantified Long terminal repeat (LTR) transcripts via digital droplet polymerase chain reaction (ddPCR) for HIV-infected HA harvested 7 dpi with total RNA isolated with statistical significance determined by ANOVA, ** $p<0.01$ and * $p<0.05$ Post hoc analysis Dunn's test.

HIV infected HA treated with nanogel post HIV exposure exhibited 10-fold and 5-fold reduction in p24 and LTR transcripts, respectively, as shown in FIG. 2A and FIG. 2B, respectively. This evidence indicates that the nanogel significantly disrupts the HIV life cycle such that both viral transcription and release are greatly reduced.

The biopolymer-based hydrogel nanoparticles and microparticles of chitosan, hydroxyethyl cellulose (HEC), and linseed oil polyol can be used in conjunction with any appropriate vehicle for administration. In certain embodiments, the biopolymer-based hydrogel nanoparticles and microparticles of the subjection invention may be administered by inhalation, orally, intra-nasally, topically, intramuscularly, subcutaneously, intrathecally, intravenously or intraperitoneally by infusion or injection.

The biopolymer-based hydrogel nanoparticles and microparticles are preferably formulated into suitable pharmaceutical preparations such as aerosols, inhalants, tablets, capsules, or elixirs for oral administration or in sterile solutions or suspensions for parenteral administration. Typically, the biopolymer-based hydrogel nanoparticles and microparticles described above are formulated into pharmaceutical compositions using techniques and procedures known in the art.

In one embodiment, the composition comprising the biopolymer-based hydrogel nanoparticles and microparticles according to the invention, together with a conventional adjuvant, carrier, or diluent, may thus be placed into the form of solids including pills, troches, tablets, cachets, lozenges, filled capsules, powder and pellet forms, and liquids such as aqueous or non-aqueous solutions, suspensions, emulsions, elixirs, and capsules filled with the same. The composition may further comprise conventional ingredients in conventional proportions, with or without additional active compounds.

The tablets, troches, pills, capsules, and the like may also contain one or more of the following: binders such as gum tragacanth, acacia, corn starch or gelatin; excipients such as dicalcium phosphate; a disintegrating agent such as corn starch, potato starch, alginic acid, and the like; a lubricant such as magnesium stearate; and a sweetening agent such as sucrose, fructose, lactose, or aspartame, or a flavoring agent such as peppermint, oil of wintergreen, or cherry flavoring may be added. Various other materials may be present as coatings or for otherwise modifying the physical form of the solid unit dosage form. For instance, tablets, pills, or capsules may be coated with gelatin, wax, shellac, or sugar, and the like.

In one embodiment, the nanoparticles or microparticles can be used as an aqueous suspension formulation for introduction to a patient by an injection, for the topical application to an internal or external body surface, or within a liquid filled capsule. The aqueous solution can be employed in a water-in-oil emulsion wherein the continuous phase vehicle of the oil can be exploited for surface properties to retain the nanoparticle and/or microparticle formulation in a selected environment of the body. The aqueous solution can be employed in an oil-in-water emulsion wherein the continuous phase vehicle of the aqueous suspension can be augmented by oil-soluble or oil-suspendable adjuvants.

The pharmaceutical dosage forms suitable for injection or infusion can include sterile aqueous solutions or dispersions or sterile powders comprising the biopolymer-based hydrogel nanoparticles and microparticles. Preferably, the ultimate dosage form should be sterile, fluid, and stable under the conditions of manufacture and storage. The liquid carrier or vehicle can be a solvent or liquid dispersion medium comprising, for example, water, a polyol (for example, glycerol, propylene glycol, liquid polyethylene glycols, and the like), vegetable oils, nontoxic glyceryl esters, and suitable mixtures thereof.

Pharmaceutical compositions for topical administration can be formulated as ointments, creams, lotions, gels, or as a transdermal patch. Such transdermal patches can contain penetration enhancers such as linalool, carvacrol, thymol, citral, menthol, t-anethole, and the like. Ointments and creams can, for example, include an aqueous or oily base with the addition of suitable thickening agents, gelling agents, colorants, and the like. Lotions and creams can include an aqueous or oily base and typically also contain one or more emulsifying agents, stabilizing agents, dispersing agents, suspending agents, thickening agents, coloring agents, and the like. Gels preferably include an aqueous carrier base and include a gelling agent such as cross-linked polyacrylic acid polymer, a derivatized polysaccharide (e.g., carboxymethyl cellulose), and the like.

Pharmaceutical compositions suitable for intra-nasal administration are also encompassed by the present invention. Such intra-nasal compositions comprise the biopolymer-based hydrogel nanoparticles and microparticles, in a vehicle and suitable administration device to deliver a liquid spray, dispersible powder, or drops. Drops may be formulated with an aqueous or non-aqueous base also comprising one or more dispersing agents, solubilizing agents, or suspending agents. Liquid sprays are conveniently delivered from a pressurized pack, an insufflator, a nebulizer, or other convenient means of delivering an aerosol. The nanoparticles or microparticles may be combined with an inert powdered carrier and inhaled by the subject or insufflated.

Pharmaceutical compositions for administration by inhalation or insufflation can be provided in the form of a dry powder composition, and a suitable powder base such as lactose or starch. Such powder composition can be provided in unit dosage form, for example, in capsules, cartridges, gelatin packs, or blister packs, from which the powder can be administered with the aid of an inhalator or insufflator. In a preferred embodiment, the biopolymer-based hydrogel nanoparticles and microparticles are administered in an inhalant form.

The formulation can include adjuvants that include, but are not exclusive to one or more of: nutrients, surfactants, thickeners, other viscosity modifiers, fillers, and other drugs. The drugs can be other antiviral agents, antibacterial agents, antifungal agents, or any combination of one or more of these drugs.

The biopolymer-based hydrogel nanoparticles and/or microparticles formulation can be used as a prophylactic agent, such that it can be used prior to potential exposure to HIV or other viruses. For example, a suspension of the nanoparticles or microparticles can be contacted with surfaces of the genitals or other surfaces contacted during intimate contact between persons. Pills or capsules can also be ingested prior to intimate contact in a prophylactic capacity.

Alternately, the biopolymer-based hydrogel nanoparticles and/or microparticles comprising formulation can be used by a patient after contracting HIV or other viral infection.

The formulations can be used in regiments that employ other agents for compound therapies where the nanoparticle and/or microparticles are used simultaneously or non-simultaneous administration to attack the virus or relieve other symptoms or combat secondary infections with other virus, bacteria, or fungi to the compromised patient.

In one embodiment, the composition is formulated in accordance with routine procedures as a pharmaceutical composition adapted for local administration to humans. Typically, compositions for local administration are solutions in a sterile isotonic aqueous buffer. Where necessary, the composition may also include a solubilizing agent and a local anesthetic such as lidocaine to case pain at the site of the injection. Generally, the ingredients are supplied either separately or mixed together in unit dosage form, for example, as a dry lyophilized powder or water free concentrate in a hermetically sealed container such as an ampoule or sachet indicating the quantity of active agent. Where the composition is administered by injection, an ampoule of sterile water for injection or saline can be provided so that the ingredients may be mixed prior to administration.

The particular mode of administration and the dosage regimen will be selected by the attending clinician, taking into account the particulars of the case (e.g., the subject, the disease, the disease state involved, and whether the treatment is prophylactic). Treatment may involve daily or multi-daily doses of compound(s) over a period of a few days to months, or even years.

In general, however, a suitable dose will be in the range of from about 0.001 to about 100 mg/kg of body weight per day, preferably from about 0.01 to about 100 mg/kg of body weight per day, more preferably, from about 0.1 to about 50 mg/kg of body weight per day, or even more preferred, in a range of from about 1 to about 10 mg/kg of body weight per day. For example, a suitable dose may be about 1 mg/kg, 10 mg/kg, or 50 mg/kg of body weight per day.

The hydrogel nanoparticles and/or microparticles can be conveniently administered in unit dosage form, containing for example, about 0.05 to about 10000 mg, about 0.5 to about 10000 mg, about 5 to about 1000 mg, or about 50 to about 500 mg of the hydrogel nanoparticles and/or microparticles per unit dosage form.

The hydrogel nanoparticles and/or microparticles may conveniently be presented in a single dose or as divided doses administered at appropriate intervals, for example, as one dose per day or as two, three, four or more sub-doses per day. The sub-dose itself may be further divided, e.g., into a number of discrete loosely spaced administrations.

Optionally, the pharmaceutical compositions of the present invention can include one or more other therapeutic agents, e.g., as a combination therapy. The additional therapeutic agent(s) will be included in the compositions within a therapeutically useful and effective concentration range, as determined by routine methods that are well known in the medical and pharmaceutical arts. The concentration of any particular additional therapeutic agent may be in the same range as is typical for use of that agent as a monotherapy, or the concentration may be lower than a typical monotherapy concentration if there is a synergy.

In specific embodiments, the hydrogel nanoparticles and/or microparticles are also loaded with a therapeutic agent capable of treating diseases caused by the viral infection. The therapeutic agent may also be an antagonist of opiates. The combination of the hydrogel nanoparticles and/or microparticles and an antagonist of opiates may be used as Pre-exposure prophylaxis (PrEP) agent as first line of defense for HIV, in particular, in high risk groups. Such combined therapy may have universal applicability against viral infections and offers treatment of opiate associated neuronal abnormalities and AIDS.

In one embodiment, the subject invention further provides a method for modulating the immune status of the host cells, comprising contacting the host cells with the hydrogel nanoparticles and/or microparticles of the subject invention. The hydrogel nanoparticles and/or microparticles act as nanovaccine that changes the immune response of the cells.

In one embodiment, the subject invention provides a method for drug delivery into a cell by contacting the cells with the hydrogel nanoparticles and/or microparticles of the subject invention, wherein the hydrogel nanoparticles and/or microparticles are loaded with a drug. In a preferred embodiment, the cell is, for example, microglial cells, PBMCs, neurons, astrocytes, and epithelia cells.

In one embodiment, the subject invention provides a method for inhibiting a virial replication in a host cell or macrophage, comprising contacting the host cell or macrophage with the hydrogel nanoparticles and/or microparticles or the composition of the subject invention, and optionally, the hydrogel nanoparticles and/or microparticles being loaded with a drug, e.g., an anti-viral drug, wherein the host cell or macrophage contacts with the hydrogel nanoparticles and/or microparticles or the composition of the subject invention prior to the infection by a virus, e.g., HIV.

In one embodiment, the subject invention provides a method for disrupting/inhibiting a virial replication in a host cell or marcrophage, comprising contacting the host cell with the hydrogel nanoparticles and/or microparticles or a composition according to the subjection, wherein the host cell has been infected with a virus, e.g., retrovirus such HIV, and optionally, the hydrogel nanoparticles and/or microparticles are loaded with a drug, e.g., an anti-viral drug.

In one embodiment, the subject invention provides a method for preventing and/or treating a virial infection in a host cell or macrophage, comprising contacting the host cell with the hydrogel nanoparticles and/or microparticles or a composition of the subject invention, and optionally, the hydrogel nanoparticles and/or microparticles being loaded with a drug, e.g., an anti-viral drug.

In specific embodiment, the hydrogel nanoparticles and/or microparticles contacting with the host cell or macrophage at a concentration ranging, for example, from 0.1 µg/ml to 500 µg/ml, from 1 µg/ml to 450 µg/ml, from 1 µg/ml to 400 µg/ml, from 5 µg/ml to 400 µg/ml, from 10 µg/ml to 350 µg/ml, from 10 µg/ml to 300 µg/ml, from 25 µg/ml to 250 µg/ml, from 50 µg/ml to 200 µg/ml, from 50 µg/ml to 150 µg/ml, from 75 µg/ml to 200 µg/ml, or from 100 µg/ml to 200 µg/ml.

In preferred embodiments, the hydrogel nanoparticles and/or microparticles is loaded with a therapeutic agent. The agent may be capable of, for example, treating diseases affecting the central nervous system (CNS) including, but not limited to, brain tumors, cancer, neuroAIDS, and other neurodegenerative disorders.

Non-limiting examples of drugs include natural enzymes, proteins derived from natural sources, recombinant proteins, natural peptides, synthetic peptides, cyclic peptides, antibodies, cytotoxic agents, immunoglobins, beta-adrenergic blocking agents, calcium channel blockers, coronary vasodilators, cardiac glycosides, antiarrhythmics, cardiac sympathomimetics, angiotensin converting enzyme (ACE) inhibitors, diuretics, inotropes, cholesterol and triglyceride reducers, bile acid sequestrants, fibrates, 3-hydroxy-3-methylglutaryl (HMG)-CoA reductase inhibitors, niacin derivatives, antiadrenergic agents, alpha-adrenergic blocking agents, centrally acting antiadrenergic agents, vasodilators, potassium-sparing agents, thiazides and related agents, angiotensin II receptor antagonists, peripheral vasodilators, antiandrogens, estrogens, antibiotics, retinoids, insulins and analogs, alpha-glucosidase inhibitors, biguanides, meglitinides, sulfonylureas, thiazolidinediones, androgens, progestogens, bone metabolism regulators, anterior pituitary hormones, hypothalamic hormones, posterior pituitary hormones, gonadotropins, gonadotropin-releasing hormone antagonists, ovulation stimulants, selective estrogen receptor modulators, antithyroid agents, thyroid hormones, bulk forming agents, laxatives, antiperistaltics, flora modifiers, intestinal adsorbents, intestinal anti-infectives, antianorexic, anticachexic, antibulimics, appetite suppressants, antiobesity agents, antacids, upper gastrointestinal tract agents, anticholinergic agents, aminosalicylic acid derivatives, biological response modifiers, corticosteroids, antispasmodics, 5-HT4 partial agonists, antihistamines, cannabinoids, dopamine antagonists, serotonin antagonists, cytoprotectives, histamine H2-receptor antagonists, mucosal protective agent, proton pump inhibitors, *H. pylori* eradication therapy, erythropoieses stimulants, hematopoictic agents, anemia agents, heparins, antifibrinolytics, hemostatics, blood coagulation factors, adenosine diphosphate inhibitors, glycoprotein receptor inhibitors, fibrinogen-platelet binding inhibitors, thromboxane-A2 inhibitors, plasminogen activators, antithrombotic agents, glucocorticoids, mineralcorticoids, corticosteroids, selective immunosuppressive agents, antifungals, drugs involved in prophylactic therapy, AIDS-associated infections, cytomegalovirus, non-nucleoside reverse transcriptase inhibitors, nucleoside analog reverse transcriptse inhibitors, protease inhibitors, anemia, Kaposi's sarcoma, aminoglycosides, carbapenems, cephalosporins, glycopeptides, lincosamides, macrolies, oxazolidinones, penicillins, streptogramins, sulfonamides, trimethoprim and derivatives, tetracyclines, anthelmintics, amebicides, biguanides, cinchona alkaloids, folic acid antagonists, quinoline derivatives, Pneumocystis carinii therapy, hydrazides, imidazoles, triazoles, nitroimidzaoles, cyclic amines, neuraminidase inhibitors, nucleosides, phosphate binders, cholinesterase inhibitors, adjunctive therapy, barbiturates and derivatives, benzodiazepines, gamma aminobutyric acid derivatives, hydantoin derivatives, iminostilbene derivatives, succinimide derivatives, anticonvulsants, ergot alkaloids, antimigrane preparations, biological response modifiers, carbamic acid caters, tricyclic derivatives, depolarizing agents, nondepolarizing agents, neuromuscular paralytic agents, CNS stimulants, dopaminergic reagents, monoamine oxidase inhibitors, COMT inhibitors, alkyl sulphonates, ethylenimines, imidazotetrazines, nitrogen mustard analogs, nitrosoureas, platinum-containing compounds, antimetabolites, purine analogs, pyrimidine analogs, urea derivatives, anthracyclines, actinomycins, camptothecin derivatives, epipodophyllotoxins, taxanes, vinca alkaloids and analogs, antiandrogens, antiestrogens, nonsteroidal aromatase inhibitors, protein kinase inhibitor antincoplastics, azaspirodecanedione derivatives, anxiolytics, stimulants, monoamine reuptake inhibitors, selective serotonin reuptake inhibitors, antidepressants, benzisooxazole derivatives, butyrophenone derivatives, dibenzodiazepine derivatives, dibenzothiazepine derivatives, diphenylbutylpiperidine derivatives, phenothiazines, thienobenzodiazepine derivatives, thioxanthene derivatives, allergenic extracts, nonsteroidal agents, leukotriene receptor antagonists, xanthines, endothelin receptor antagonist, prostaglandins, lung surfactants, mucolytics, antimitotics, uricosurics, xanthine oxidase inhibitors, phosphodiesterase inhibitors, metheamine salts, nitrofuran derivatives, quinolones, smooth muscle relaxants, parasympathomimetic agents, halogenated hydrocarbons, esters of amino benzoic acid, amides (e.g. lidocaine, articaine hydrochloride, bupivacaine hydrochloride), antipyretics, hynotics and sedatives, cyclopyrrolones, pyrazolopyrimidines, nonsteroidal anti-inflammatory drugs, opioids, para-aminophenol derivatives, alcohol dehydrogenase inhibitor, heparin antagonists, adsorbents, emetics, opioid antagonists, cholinesterase reactivators, nicotine replacement therapy, vitamin A analogs and antagonists, vitamin B analogs and antagonists, vitamin C analogs and antagonists, vitamin D analogs and antagonists, vitamin E analogs and antagonists, and vitamin K analogs and antagonists.

As used herein, the singular forms "a," "an," and "the" are intended to include the plural forms as well, unless the context clearly indicates otherwise. Furthermore, to the extent that the terms "including," "includes," "having," "has," "with," or variants thereof are used in either the detailed description and/or the claims, such terms are intended to be inclusive in a manner similar to the term "comprising." The transitional terms/phrases (and any grammatical variations thereof) "comprising," "comprises," and "comprise" can be used interchangeably; "consisting essentially of," and "consists essentially of" can be used interchangeably; and "consisting," and "consists" can be used interchangeably.

The transitional term "comprising," "comprises," or "comprise" is inclusive or open-ended and does not exclude additional, unrecited elements or method steps. By contrast, the transitional phrase "consisting of" excludes any element, step, or ingredient not specified in the claim. The phrases "consisting" or "consists essentially of" indicate that the claim encompasses embodiments containing the specified materials or steps and those that do not materially affect the basic and novel characteristic(s) of the claim. Use of the term "comprising" contemplates other embodiments that "consist" or "consisting essentially of" the recited component(s).

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 0-20%, 0 to 10%, 0 to 5%, or up to 1% of a given value. Where particular values are described in the application and claims, unless otherwise stated the term "about" meaning within an acceptable error range for the particular value should be assumed.

When ranges are used herein, such as for dose ranges, combinations and subcombinations of ranges (e.g., subranges within the disclosed range), specific embodiments therein are intended to be explicitly included.

Methods and Materials

Chitosan (448877-50G, Sigma Aldrich), HEC (22-300 mPa·s, 2% in water at 20° C., TCI, 9004-62-0), Heavy liquid paraffin oil (0.8660-0.890 g/cm$^3$), Tween 80, Ethanol, n-Hexane (Sigma Aldrich), Glycine (75.07 g/mol, 1.607 g/cm$^3$), linseed oil, glacial acetic acids, hydrogen peroxide, diethylether, and acetic anhydride (Sigma Aldrich) were used as received. Linseed oil polyol was prepared using the method of Sharmin et al., *International Journal of Biological Macromolecules*, 2007, 40, 407-22. Deionised water from a Millipore mille U10 water purification system was used in the preparation of hydrogels and other In vitro experiments.

Preparation of Micro/Nanogels

Hydrogel nanoparticles of chitosan (0.7 g) and HEC (0.3 g) with linseed oil based polyol as a hydrophobic modifier (1 ml of 2%), were prepared in a beaker using a water-in-oil emulsion polymerization method. Polymer solution (20 ml) of 2% (w/v)) was prepared in 1% (v/v) acetic acid. A separate beaker was used to make a mixture of liquid paraffin oil and 1% (w/w) Tween 80. The polymer solution was added dropwise to the mixture of oil and surfactant stirred at 14000 rpm on a magnetic stirrer. The mixing of the solution was continued for 20 minutes followed by the addition of glutaraldehyde (5 ml) for another 10 minutes. The linseed oil polyol was added to the reaction mixture and stirring was continued at 14000 rpm for 5 hours. The particles were washed thoroughly with n-hexane to remove excess oil. Any excess glutaraldehyde was deactivated by 0.1 M glycine. The washed hydrogel particles were dried at room temperature. A TEM image of the nanoparticles is shown in FIG. 3.

Characterization of Micro/Nanogels Using FT-IR, Raman and TEM Analysis

The hydrogel samples were dried under vacuum overnight till attaining a constant weight. The dried samples were analyzed using model 1750 FT-IR spectrophotometer (PerkinElmer Cetus Instruments, Norwalk, CT). TEM analysis was performed using Phillips CM-200 200 kV transmission electron microscope with an operating voltage of 80 kV.

Isolation and Culture of PBMC, Microglial (CHME5) and HA

PBMCs isolation was carried out using leukopacks (buffy coat), obtained commercially from a community blood bank (One Blood, Miami, FL, USA). PBMCs were isolated using a common protocol (see Atluri et al. *Scientific Reports*, 2016, 6, 27864). The buffy coat is diluted with PBS (Invitrogen, Gaithersburg, MD) at room temperature. The diluted whole blood was overlaid on the top of a Ficoll-Histopaque centrifuge such that three separate layers—plasma, buffy coat, and red blood cells (RBCs) were formed. The samples were centrifuged at 1,200 g for about 40 min at room temperature. The buffy coat layer formed at the interface of plasma and red blood cells. The buffy coat containing PBMCs collected and the cells were washed with PBS. The pellet was re-suspended in Ammonium-Chloride-Potassium (ACK) lysing buffer in order to lyse the RBCs in the samples. The suspension was kept in ice for 15 minutes. Cells were washed a second time with PBS. The total cell number and cell viability was evaluated by trypan blue (Sigma, St. Louis, MO) exclusion. The PBMC pellet were re-suspended in a culture medium of Roswell Park Memorial Institute (RPMI) 1640 (Life Technologies, Gaithersburg, MD), 25 mM 4-(2-hydroxyethyl)-1-piperazineethanesulfonic acid (HEPES) (Sigma, St. Louis, MO), 2 mM glutamine (Sigma, St. Louis, MO), 100 µg streptomycin (Sigma, St. Louis, MO), 100 U penicillin (Sigma, St. Louis, MO), and 10% fetal bovine serum (Life Technologies, Gaithersburg, MD).

CHME5, a microglia cell line was cultured using Eagle's minimum essential medium (MEM) supplemented by fetal bovine serum to a final concentration of the antibiotic/antimycotic solution (Sigma-Aldrich, St. Louis, MO).

Primary HAs were purchased from ScienCell Research laboratories (Carlsbad, CA; Cat. #1800-5). These cells were grown on the astrocyte medium purchased from ScienCell laboratories (Cat. #1801) containing 2% of fetal bovine serum (ScienCell Cat. #0010), astrocyte growth supplement (ScienCell Cat. #1852) and penicillin/streptomycin (ScienCell Cat. #0503), antibiotic/antimycotic solution (Sigma-Aldrich, St. Louis, MO).

Biocompatibility Assessment

Figure 4A:
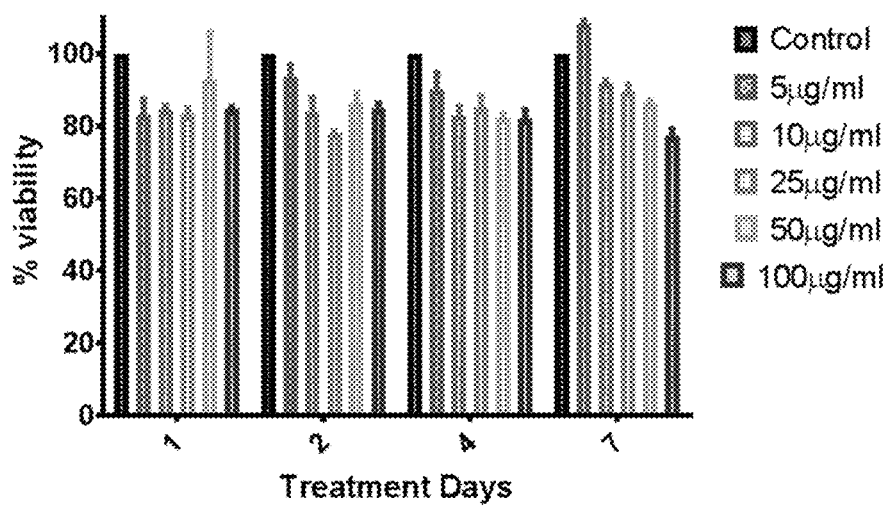
FIG. 4A shows a bar graph of cytocompatibility testing for nanogels at various concentrations (5-100 μg/ml) as a function of time for HAs.
Figure 4B:
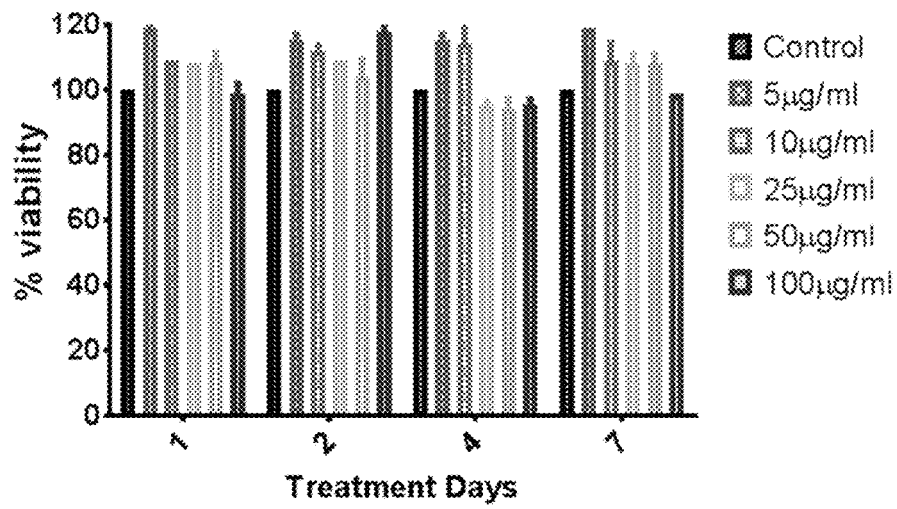
FIG. 4B shows a bar graph of cytocompatability testing for nanogels at various concentrations (5-100 μg/ml) as a function of time for PBMCs.
Figure 4C:
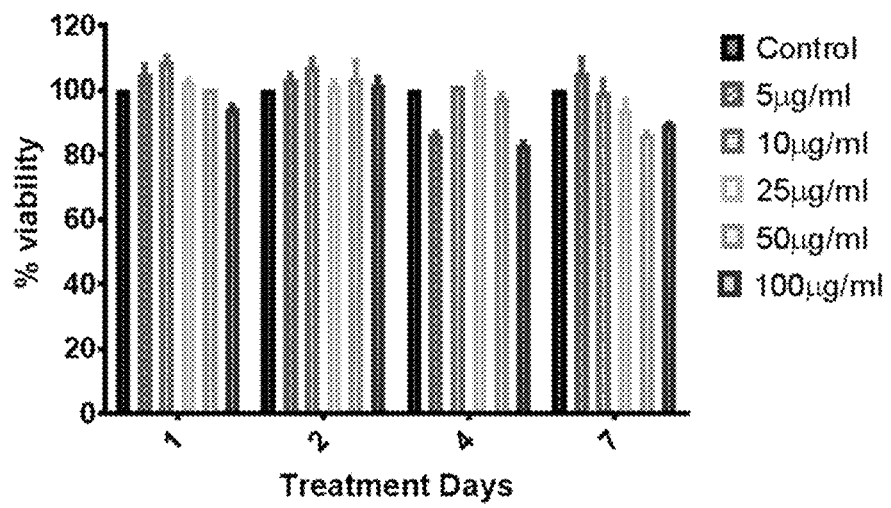
FIG. 4C shows a bar graph of cytocompatibility testing for nanogels at various concentrations (5-100 μg/ml) as a function of time for CHME-5.

Biocompatibility was assessed for HAs, PBMCs and CHME5 using a XTT cell viability assay with sodium 3,3'-(-[(phenlamino)carbonyl]-3,4-tetrazolium)-bis(4-methoxyl-6-nitro)benzene sulfonic acid hydrate, as shown in FIGS. 4A-4C, respectively. Primary HAs (1×104 cells per well) were seeded in a 24 well plate and after 24 h of incubation at 37° C., the medium was replaced with 1 ml of fresh medium containing nanogel 5-100 ug/ml. Cells were treated with various concentrations and incubated for 1, 2, 4, and 7 days. XTT, 1 mg/ml, and 2.5 µl of freshly prepared phenazinemethosulfate (PMS) solution were added to each well.

The XTT containing wells were incubated for 4 hours at 37° C. A multi-mode microplate reader (Synergy HT), was used to measure absorbance at 450 nm wavelength. All experiments were performed in triplicate. Statistical analysis was performed as a one-way analysis of variance (ANOVA) and using Tukey's multiple comparison test and difference considered was $P<0.05$.

CHME5 and PBMCs, 2×10$^5$ cells per well were seeded in 24 well plate. The protocol described above for HAs was followed for each cell type. To maintain the PBMCs for 7 days, fresh media containing IL-2 was added at regular intervals.

Lactate Dehydrogenase (LDH) Cytotoxicity of Nanogel in CHME5 and PBMCs

CHME5 cells and PBMCs (10,000 cells per well) were plated in a 96-well plate and incubated at 37° C., 5% $CO_2$. After 24 hrs, different concentrations (10-100 µg/ml) of nanogel formulations were added to the culture media and incubated for 24 hrs. The Thermo Scientific Pierce LDH Cytotoxicity Assay Kit was used to quantitatively measure lactate dehydrogenase (LDH) released into the media from damaged cells, which act as a biomarker for the cellular cytotoxicity and cytolysis. For the determination of the LDH background activity, a complete medium control was included. Additional cells were plated in triplicate for spontaneous LDH activity controls (negative control with water) and maximum LDH activity controls (positive control with 10× lysis buffer). Plates were incubated overnight in $CO_2$ at 37° C. Various concentrations of nanogels were prepared (10-100 µg/ml) and added to one set of wells. Further, cells were incubated for 24 hours in an incubator at 37° C., 5% $CO_2$. 10 µL of Lysis Buffer (10×) was added to the wells serving as Maximum LDH Activity Controls and mixed gently by tapping. The plate was further incubated at 37° C., 5% $CO_2$ for 45 minutes. A 50 µL portion of each sample medium (e.g., complete medium, serum-free medium, Spontaneous LDH Activity Controls, compound-treated and Maximum LDH Activity Controls) was transferred to a 96-well flat-bottom plate in triplicate wells using a multichannel pipette. The plate is incubated at room temperature for 30 minutes in dark.

After 30 minutes of incubation, 50 μL of stop solution was added to each sample well and mixed gently by tapping. Absorbance was measured at 490 nm and 680 nm. Determination of LDH activity was done by subtracting the 680 nm absorbance value from (background) from the 490 nm absorbance before calculation of % Cytotoxicity.

% Cytotoxicity=Nanogels treated LDH activity-Spontaneous LDH activity/Maximum LDH—Spontaneous-LDH Nanogels treated×100.

% Cytotoxicity=Compound-treated LDH activity-Spontaneous LDH activity/Maximum LDH activity-Spontaneous LDH activity×100.

Cellular Uptake

CHME5 and PBMCs cells (1×106) were incubated for 24 hours in different concentrations of nanogels (1 to 100 μg/ml). The cells were harvested, washed, and data acquired using Amnis FlowSight and analyzed using Ideas Software. A total of 10,000 events were collected for all samples. Since these nanogels have multichannel fluorescence properties, they were acquired and analyzed through predetermined channel 8 (ex/em: 405 nm/505-560 nm) that demonstrated the maximum intensity.

Differentiation of Macrophages

Whole blood was acquired from Oneblood.org and the peripheral blood mononuclear cells (PBMCs) were isolated using Ficoll-Hypaque and placed in T-75 flask and allowed to adhere for 4 hours. Non-adherent-PBMCs were removed from the flask. The remaining adherent PBMCs were cultured for an additional 5 days in growth medium supplemented with M-CSF for the macrophage differentiation. For the Pre-Infection: Differentiated macrophages were pre-treated with increasing dosing of nanogels (1-100 μg/ml). for 16 hours and then infected with HIV (overnight), non-attached virus removed by PBS wash, and cell cultured with growth medium. For the post infection: Macrophages were first infected with HIV (overnight), washed with PBS post-infection, and increasing doses of nanogels (1-100 μg/ml) were added to culture media. Supernatants were collected 7, 10, and 15 days post-infection (dpi) and HIV replication was measured by p24 ELISA.

Two-Photon Imaging $1\times10^6$ cells were plated on a 2-chamber slide until cells reached about 80% confluency. The cells were treated with 50 μg/ml of nanogel concentration and incubated for different time points 6 and 24 h at 37° C., 5% CO2. The control and nanogel treated cells were washed thoroughly using PBS (pH 7.4) and further fixed using 4% paraformaldehyde solution for 20 min. Further, the cells were washed 3 times with 1× buffer with gentle agitation for 5 min and stored at −80° C. prior to imaging.

Two-photon excitation fluorescence imaging with linear confocal channel was used to visualize the uptake of nanogels by primary microglial cells. The laser scanning imaging system was custom built on Thorlabs Cerna microscope chassis (Thorlabs Inc., Newton, NJ, United States) with broadband femtosecond Ti:Sapphire laser (800 nm central wavelength, 85 MHz repetition rate, Element 600, Femtolasers, Vienna, Austria) as an excitation/illumination source. Confocal linear reflectance and TPEF images were acquired reconstructed using data acquisition board (NI PCIe-6351, Austin, TX, United States) from photomultiplier tube detectors (PMT, Hamamatsu, Japan) signals with suitable optical bandpass filters (775-785 nm for confocal; 465-495 nm and 550-633 nm for TPEF, Semrock, Rochester, NY, United States) at 1.33 frames per second by averaging 120 frames.

PMT control voltages for the respective acquisition channels were kept constant between imaging sessions of control and treated samples, while the average laser power was adjusted in the range from 5 to 20 mW. All the acquired data in confocal and TPEF channels were normalized to a maximum value between nanogels treated and control (untreated) samples, final images depict square root of the intensity for visualization purposes. The concentration of nanogel (50 μg/ml) was selected based on the other experiments (flow cytometry) as the optimum concentration to see the time based uptake by the primary microglial cells.

Statistical Analysis

Test data were represented as Mean±SD of three independent experiments or otherwise indicated. Statistical significance between the two groups determined using Student t-Test and for multiple experimental groups. One-way ANOVA was used to analyze the significant differences. Samples were considered statistically significantly when p-values equal less than 0.05.

Example 1—Nanogel Treatment of Primary Macrophage Disrupts HIV Replication

Figure 5:
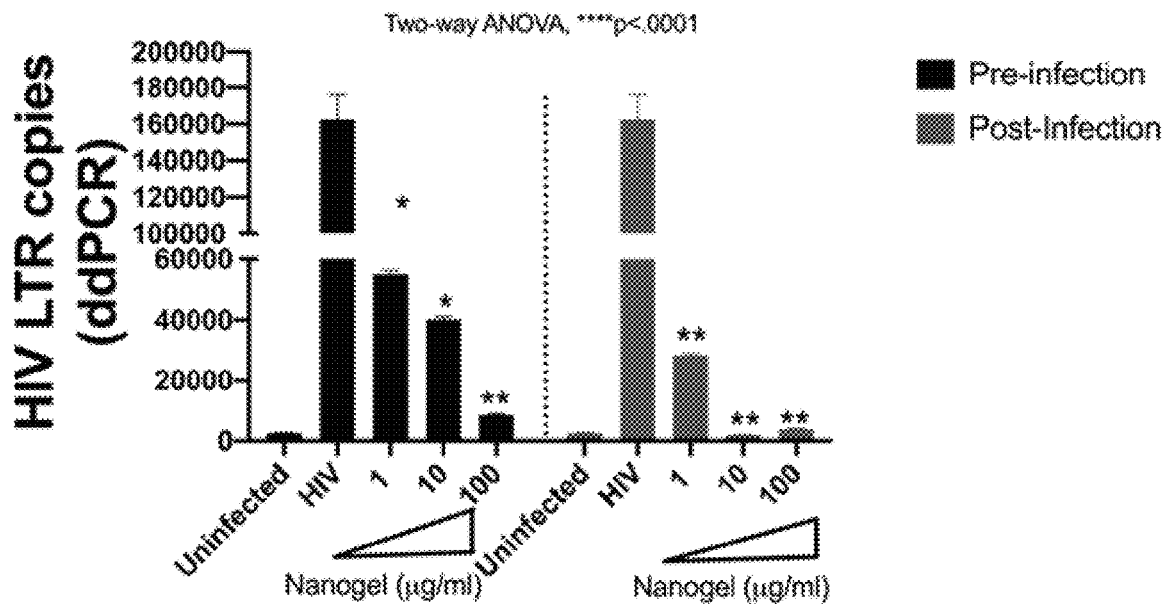
FIG. 5 shows nanogel treatment of primary macrophage disrupting HIV replication. Whole blood was acquired from Oneblood.org and PBMCs isolated using Ficoll-Hypaque and placed in T-75 cm² flask for 4 hours. Non-Adherent-PBMCs were removed from flask after 4 hours. The remaining adherent PBMCs were cultured with macrophage colony-stimulating factor (M-CSF) for an additional 5 days for macrophage differentiation. (Black bars) Differentiated macrophage were pre-treated with increasing doses of nanogel (1, 10, 100 μg/ml) for 16 hours and then infected with HIV (JR-CSF strain). Cells were harvested 15 days post infection (dpi) and digital droplet PCR (ddPCR) used to measure HIV LTR copies. (Pink bars) Macrophage were infected with HIV first (overnight adsorption), washed then treated with increasing doses of Nanogel. As above, cells were harvested 15 dpi and HIV LTR copies measured via ddPCR. Samples were compared to HIV (no treatment). Statistical significance was determined via Two-way ANOVA and Tukey's post hoc analysis, *$p>0.05$, **$p>0.01$.

Differentiated macrophage were pre-treated with increasing doses of nanogel (1, 10, 100 μg/ml) for 16 hours and then infected with HIV (JR-CSF strain). The result shows that the nanogel pretreatment disrupts HIV replication in primary macrophage in a dose-dependent manner (FIG. 5).

Figure 6A:
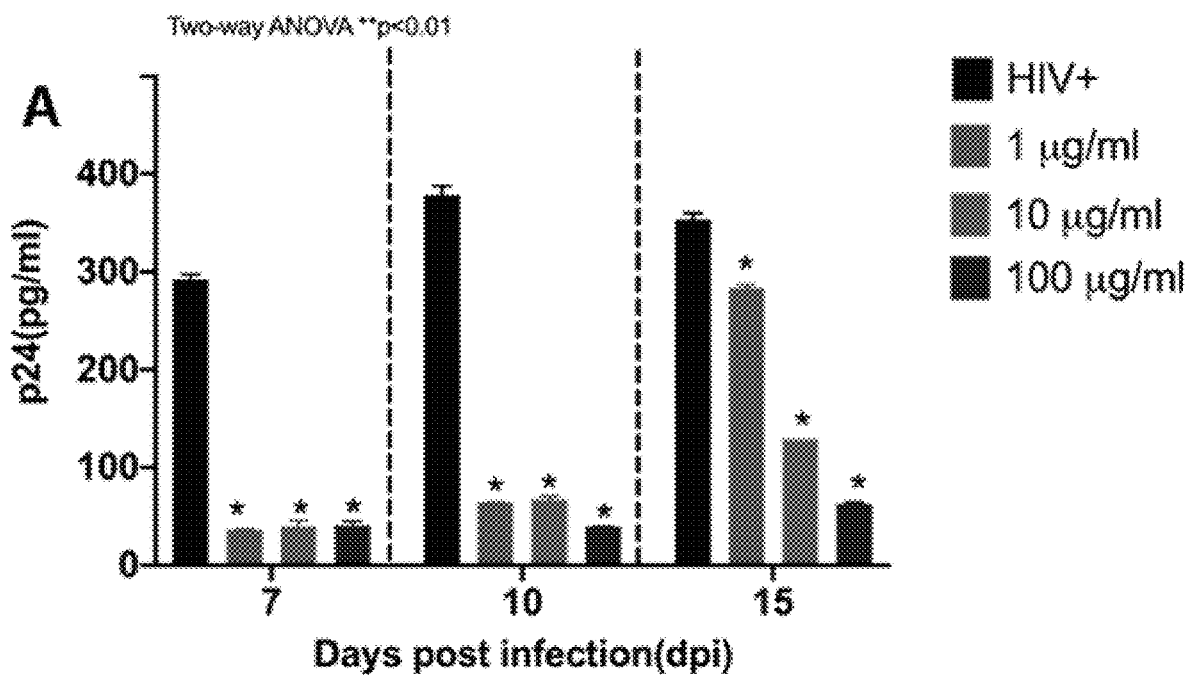
FIG. 6A shows nanogel pre-treatment inhibiting HIV replication in primary macrophage. PBMCs isolated from whole blood using Ficoll-Hypaque were cultured in T75 cm² and macrophage differentiated as described in FIG. 5. Macrophage were pre-treated with increasing doses of nanogel (1, 10, 100 μg/ml) for 1 hour and then infected with HIV (JR-CSF strain). Supernatants were collected 7, 10, and 15 dpi and HIV replication was measured by p24 ELISA. Samples were compared to HIV (no treatment). Statistical significance was determined via Two-way ANOVA and Tukey's post hoc analysis, *$p>0.05$.
Figure 6B:
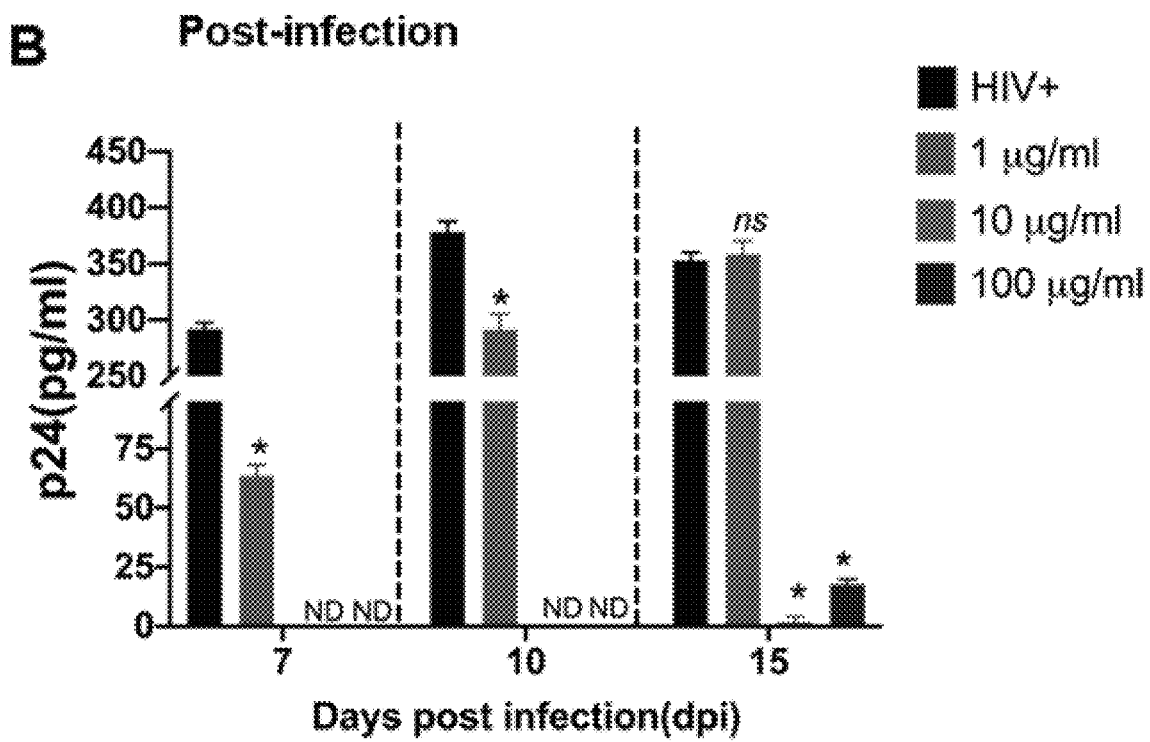
FIG. 6B shows nanogel post-treatment inhibiting HIV replication in primary macrophage. PBMCs isolated from whole blood using Ficoll-Hypaque were cultured in T75 cm² and macrophage differentiated as described in FIG. 5. Macrophage were post-treated with nanogels (1, 10, 100 μg/ml) after virus adsorption. Supernatants were collected 7, 10, and 15 dpi and HIV replication was measured by p24 ELISA. Samples were compared to HIV (no treatment). Statistical significance was determined via Two-way ANOVA and Tukey's post hoc analysis, *$p>0.05$.
Figure 7A:
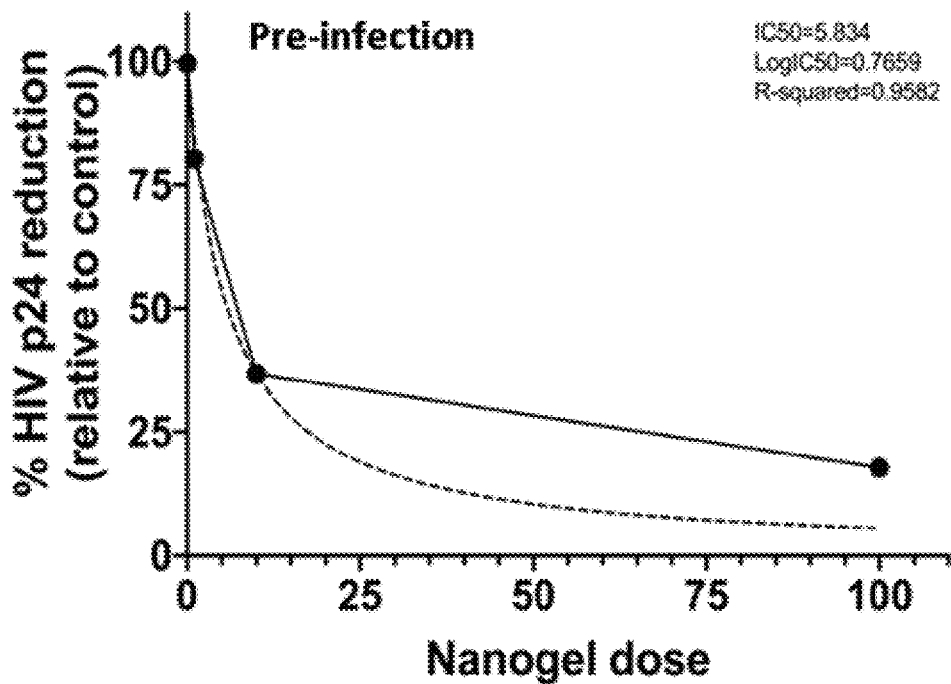
FIG. 7A shows nanogel inhibition of HIV replication in primary macrophage. Non-linear regression of p24 values normalized to the untreated control. The macrophage were pre-treated with increasing doses of nanogel (1, 10, 100 μg/ml) for 16 hours, infected with HIV (JR-CSF strain). Supernatants were collected 7, 10, and 15 dpi and HIV replication was measured by p24 ELISA. The 15 dpi samples were normalized to the untreated control to yield % HIV p24 reduction. Non-linear regression analysis performed to determine the IC50. Samples were compared to HIV (no treatment). Statistical significance was determined via Two-way ANOVA and Tukey's post hoc analysis, *$p>0.05$.
Figure 7B:
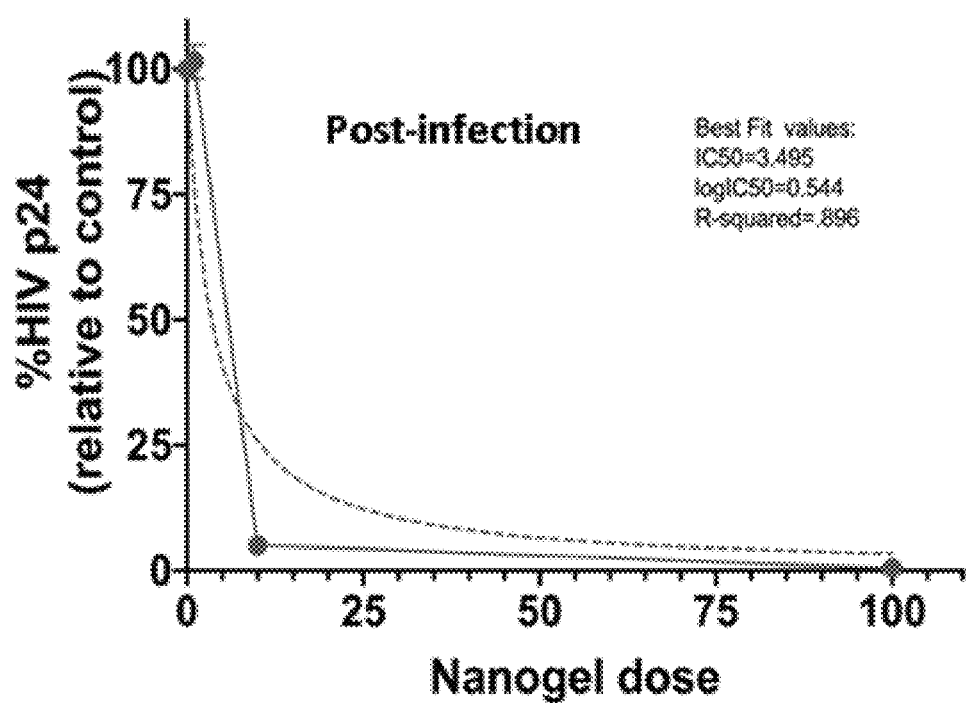
FIG. 7B shows nanogel inhibition of HIV replication in primary macrophage. Non-linear regression of p24 values normalized to the untreated control. The macrophage were post-treated with increasing doses of nanogel (1, 10, 100 μg/ml) for 16 hours, infected with HIV (JR-CSF strain). Supernatants were collected 7, 10, and 15 dpi and HIV replication was measured by p24 ELISA. The 15 dpi samples were normalized to the untreated control to yield % HIV p24 reduction. Non-linear regression analysis performed to determine the IC50. Samples compared to HIV (no treatment). Statistical significance determined via Two-way ANOVA and Tukey's post hoc analysis, *$p>0.05$.

Macrophage infected with HIV were treated with increasing doses of Nanogel (1, 10, 100 μg/ml). Such treatment significantly inhibits HIV replication in primary macrophage (FIG. 5). Consistent results can be found in FIGS. 6 and 7.

Example 2—Two-Photon Imaging

Figures 8A, 8B:
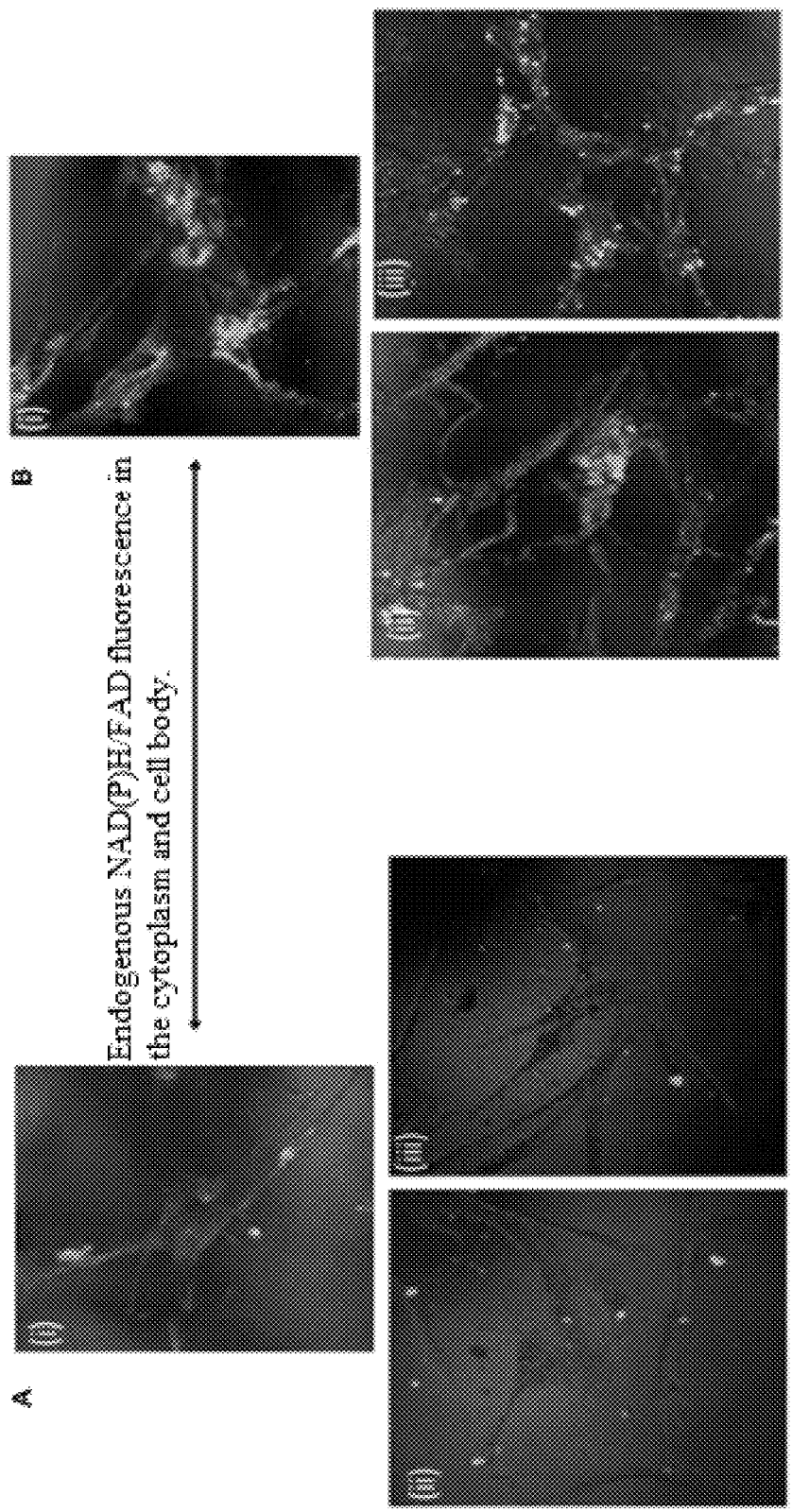
FIG. 8A shows the combined reflectance confocal and two-photon imaging of nanogel uptake by Primary microglial cells at (i) Control; (ii,iii) 6 h treatment of nanogels. Pseudocoloring: Red—confocal (or nearly confocal) reflectance at 780 nm; Green—Two-photon excitation fluorescence (400-633 nm range all together). Average laser power ranging from 5 to 20 mW.
FIG. 8B shows the combined reflectance confocal and two-photon imaging of nanogel uptake by Primary microglial cells at (i) Control; (ii, iii) 24 h treatment of nanogels. Pseudocoloring: Red—confocal (or nearly confocal) reflectance at 780 nm; Green—Two-photon excitation fluorescence (400-633 nm range all together). Average laser power ranging from 5 to 20 mW.

The two-photon fluorescence imaging confirmed the cellular uptake of nanogels for up to 24 h. FIG. 8 showed the 6 and 24 h time-based uptake of nanogel by primary microglial cells. Control (untreated) and nanogel treated cells were imaged and are depicted in FIG. 8. The time-based uptake showed that there was increased uptake of nanogels in 24 h. Please note that the untreated cells have background endogenous fluorescence (FIG. 8), which is due to the presence of NADH/FAD fluorescent co-factors in the cytoplasm and cell body. The imaging technique showed the presence of fluorescent nanogel particle in primary microglial cells in 465-495 nm and 550-633 nm channels.

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

We claim:

1. A method of treatment for a viral infection, comprising administering to a subject in need of such treatment biopolymer-based hydrogel nanoparticles, said biopolymer-based hydrogel nanoparticles having a core-shell structure and comprising one or more biopolymers selected from hydroxylpropylcellulose (HPC), carboxymethyl cellulose (CMC), methyl cellulose (MC), starches, pectin, chitosan, and hydroxyethyl cellulose (HEC), and linseed oil polyol.

2. The method according to claim 1, the one or more biopolymers being selected from chitosan, and HEC.

3. The method according to claim 1, the administration comprising applying an aqueous suspension comprising said biopolymer-based hydrogel nanoparticles.

4. The method according to claim 3, the aqueous suspension comprising said biopolymer-based hydrogel nanoparticles being within a water-in-oil emulsion.

5. The method according to claim 3, the aqueous suspension further comprising a second antiviral agent, an antibacterial agent, an antifungal agent, or any combination thereof.

6. The method according to claim 1, the biopolymer-based hydrogel nanoparticles being administered by inhalation, orally, topically, intra-nasally, intramuscularly, subcutaneously, intrathecally, intravenously or intraperitoneally.

7. The method according to claim 1, the biopolymer-based hydrogel nanoparticles being formulated in the form of a powder, pill, or capsule.

8. The method according to claim 1, the viral infection being a retrovirus or coronavirus infection.

9. The method according to claim 1, the viral infection being an HIV infection.

10. The method according to claim 1, the biopolymer-based hydrogel nanoparticles comprising chitosan, HEC, and a linseed oil polyol.

11. A method for inhibiting the replication of a virus in a host cell, comprising contacting the host cell with biopolymer-based hydrogel nanoparticles, said biopolymer-based hydrogel nanoparticles having a core-shell structure and comprising chitosan, HEC, and linseed oil polyol.

12. The method of claim 11, the virus being HIV.

13. The method of claim 11, contacting the host cell with the biopolymer-based hydrogel nanoparticles occurring before or after the viral infection of the host cell.

* * * * *